US009417176B2

(12) United States Patent
Arvinte

(10) Patent No.: US 9,417,176 B2
(45) Date of Patent: Aug. 16, 2016

(54) METHOD AND APPARATUS FOR DETECTING AND REGISTERING PROPERTIES OF SAMPLES

(76) Inventor: Tudor Arvinte, Riehen (CH)

( * ) Notice: Subject to any disclaimer, the term of this patent is extended or adjusted under 35 U.S.C. 154(b) by 162 days.

(21) Appl. No.: 12/522,877

(22) PCT Filed: Jan. 19, 2007

(86) PCT No.: PCT/CH2007/000025
§ 371 (c)(1),
(2), (4) Date: Jul. 10, 2009

(87) PCT Pub. No.: WO2008/086632
PCT Pub. Date: Jul. 24, 2008

(65) Prior Publication Data
US 2010/0102247 A1    Apr. 29, 2010

(51) Int. Cl.
| | | |
|---|---|---|
| *G01N 15/02* | (2006.01) | |
| *G01N 21/15* | (2006.01) | |
| *G01N 21/51* | (2006.01) | |
| *G01N 21/64* | (2006.01) | |
| *G01N 21/05* | (2006.01) | |
| *G01N 21/19* | (2006.01) | |
| *G01N 21/53* | (2006.01) | |
| *G01N 21/03* | (2006.01) | |

(52) U.S. Cl.
CPC ............ *G01N 15/0227* (2013.01); *G01N 21/51* (2013.01); *G01N 21/6402* (2013.01); *G01N 21/05* (2013.01); *G01N 21/19* (2013.01); *G01N 21/53* (2013.01); *G01N 2015/0294* (2013.01); *G01N 2021/0346* (2013.01); *G01N 2021/6417* (2013.01)

(58) Field of Classification Search
CPC .............. G01N 15/0227; G01N 21/51; G01N 21/6402; G01N 15/02
USPC ........................ 436/164, 172; 250/432 R, 428
See application file for complete search history.

(56) References Cited

U.S. PATENT DOCUMENTS

| | | | | |
|---|---|---|---|---|
| 3,624,835 | A | * 11/1971 | Wyatt ............................. 356/343 |
| 4,221,961 | A | * 9/1980 | Peyton ............... G01N 21/9018 250/223 B |
| 5,436,979 | A | * 7/1995 | Gray ........................ G06T 5/20 348/92 |
| 5,486,693 | A |   1/1996 | Achter et al. |
| 5,938,908 | A | * 8/1999 | Anazawa et al. ............. 204/603 |

(Continued)

FOREIGN PATENT DOCUMENTS

| | | |
|---|---|---|
| DE | 4223269 A1 | 1/1994 |
| GB | 2312505 A | 10/1997 |

(Continued)

OTHER PUBLICATIONS

Capelle, Martinus et al., "High throughput screening of protein formulation stability: Practical considerations" European Journal of Pharmaceutics and Biopharmaceutics, vol. 65, Jan. 5, 2007, pp. 131-148.

(Continued)

*Primary Examiner* — Christine T Mui
(74) *Attorney, Agent, or Firm* — Birch, Stewart, Kolasch & Birch, LLP

(57) ABSTRACT

A laser beam (4) is guided onto or through a sample (1) which while exposed to the laser is scanned by means of a digital scanner (2). The apparatus for performing this method comprises a laser light source (3) and a digital scanner (2).

10 Claims, 14 Drawing Sheets

(56) References Cited

U.S. PATENT DOCUMENTS

| | | | |
|---|---|---|---|
| 6,214,560 B1 * | 4/2001 | Yguerabide | C12Q 1/6816 422/50 |
| 2002/0063215 A1 | 5/2002 | Yagita | |
| 2002/0168784 A1 | 11/2002 | Sundrehagen et al. | |

FOREIGN PATENT DOCUMENTS

| | | |
|---|---|---|
| WO | WO 82/00354 A1 | 2/1982 |
| WO | WO 89/07255 A1 | 8/1989 |
| WO | WO 2006/023470 A1 | 3/2006 |

OTHER PUBLICATIONS

Demeule, Barthelemy et al., "Characterization of protein aggregation: The case of a therapeutic immunoglobulin", Biochemica et Biophysica Acta (BBA)—Proteins & Proteomics, vol. 1774, No. 1, Jan. 9, 2007, pp. 146-153.

International Search Report dated Oct. 1, 2007 for the corresponding International Application No. PCT/CH2007/000025 (Publication No. WO 2008/086632 A1).

* cited by examiner

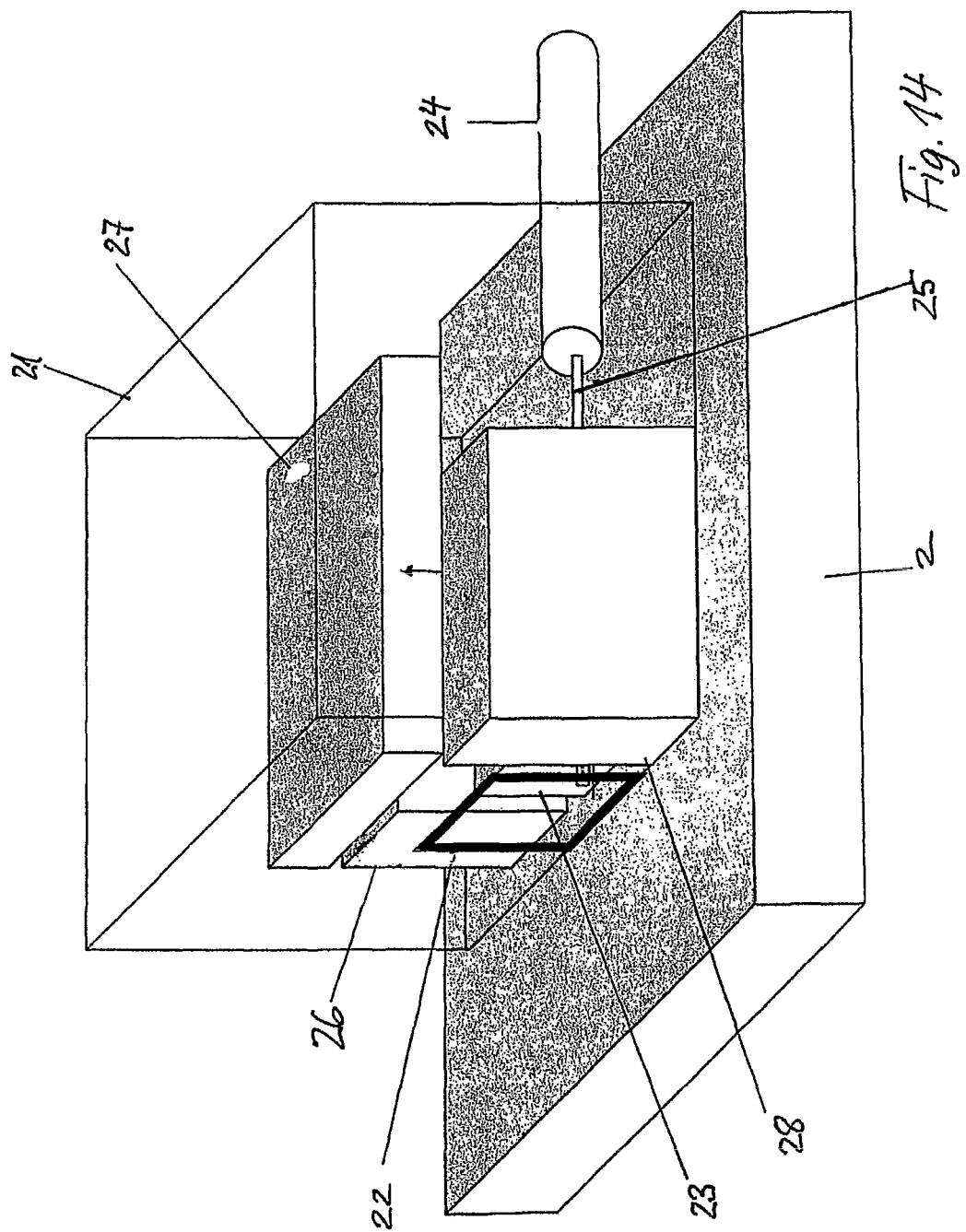

METHOD AND APPARATUS FOR DETECTING AND REGISTERING PROPERTIES OF SAMPLES

The invention relates to a method of detecting and storing information on properties of an analytical sample solution, especially a pharmaceutical preparation, by means of a digital scanning device and to an apparatus for performing this method.

Evaluation of analytical samples by means of a flat bed scanner or other electro-optical device is known. In WO 89/07255 extracting of information on chemical or biological assays or procedures, in particular the analysis of blood samples etc. by means of a flat bed scanner is disclosed. In US 2002/0168784 a diagnostic system using a flat bed scanner, especially determining and storing the result of agglutination assays is disclosed. The optical properties which are detected are fluorescence, colour, light scattering or characteristics of samples and resulting agglutinates.

For all these known methods the sample cuvettes, preferably in the form of micro titer plates are placed on the scanner bed and exposed to incident light.

It has been found that by exposing a sample to a laser beam optical effects are generated which contain information on the properties of the sample and that by digitally scanning the optical effects the information is stored and available for electronic evaluation.

Therefore, the invention is directed to an analytical method in which a laser beam is guided onto or through a sample which while exposed to the laser is scanned by means of a digital scanner. Further the invention is directed to an apparatus for performing this method comprising a light source positioned for guiding a laser beam onto or through a sample and a digital scanner arranged in a relative position to the sample for scanning the optical effect generated by the laser beam on or in the sample.

Figure 1:
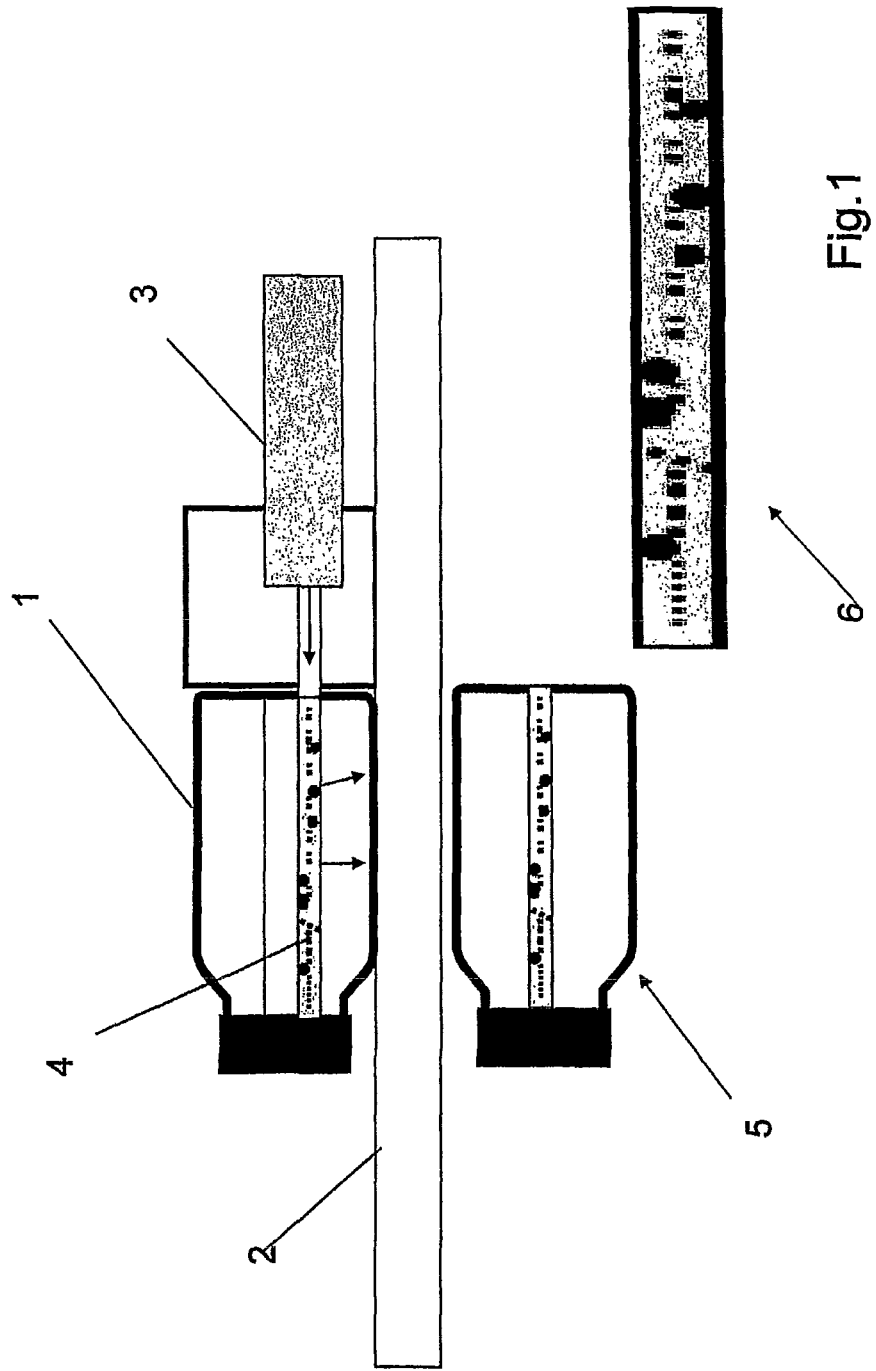

In the following preferred embodiments of the invention are described by reference to the accompanying drawings. It is shown in FIG. 1 an arrangement for analyzing a horizontally positioned vial FIG. 2 an arrangement for analyzing a vertically positioned vial FIG. 3 a multiple laser arrangement for one sample FIG. 4 an arrangement for a number of samples and lasers FIG. 5 the analysis of several samples with one laser FIG. 6 fluorescence spectroscopy in addition to laser excitation FIG. 7 on-line analysis of aggregates in vials FIG. 8 on-line analysis of aggregates in syringes FIG. 9 on-line analysis of aggregates in horizontally positioned syringes FIG. 10 a spectrofluorimeter arrangement FIG. 11 a flow-through device for liquid chromatography FIG. 12 a flow-through device for liquid chromatography with fluorescence detection FIG. 13 a flow-through device as part of a scattering detector FIG. 14 a device containing fluorescence and UV spectrometer to be placed on a scanner surface In all embodiments of the invention described hereafter a highly focussed light beam such as the beam of lasers, nano-LEDs etc. is used for excitation and visualization of particles in solutions. The use of a laser beam together with the magnification of the image by the scanner permits the visualization and analysis of particles that scatter the laser beam in the solution. Parameters like size, morphology and number of particles of defined size such as protein aggregates and/or leachables in a given volume can be determined. Red lasers are preferred for the detection of larger particles, whereas the use of green and blue lasers permits detection of smaller particles.

Containers 1 such as vials, cuvettes, multiple well plates such as micro-titer plates, syringes etc. containing sample solutions to be analyzed are positioned on or adjacent the surface of a flat bed scanner 2 and exposed to a laser beam 4 generated by a laser 3 located at the side of the scanner. As shown in FIG. 1 a vial is positioned horizontally on the scanner bed and beam 4 emitted by laser 3 enters the vial through its bottom. If the solution contained in the vial is contaminated with particles the laser beam is scattered. Scattering is effected by each individual particle in the solution. The optical effect generated by the scattering of the laser beam or, in other words, the image of the beam in the solution is digitally scanned resulting in the image 5 shown below the scanner. Electronic magnification results in a magnified image 6 showing individual particles. By means of image processing methods known as such, the particles may be analyzed by counting, classification by size, morphology, size distribution etc.

Figure 2:
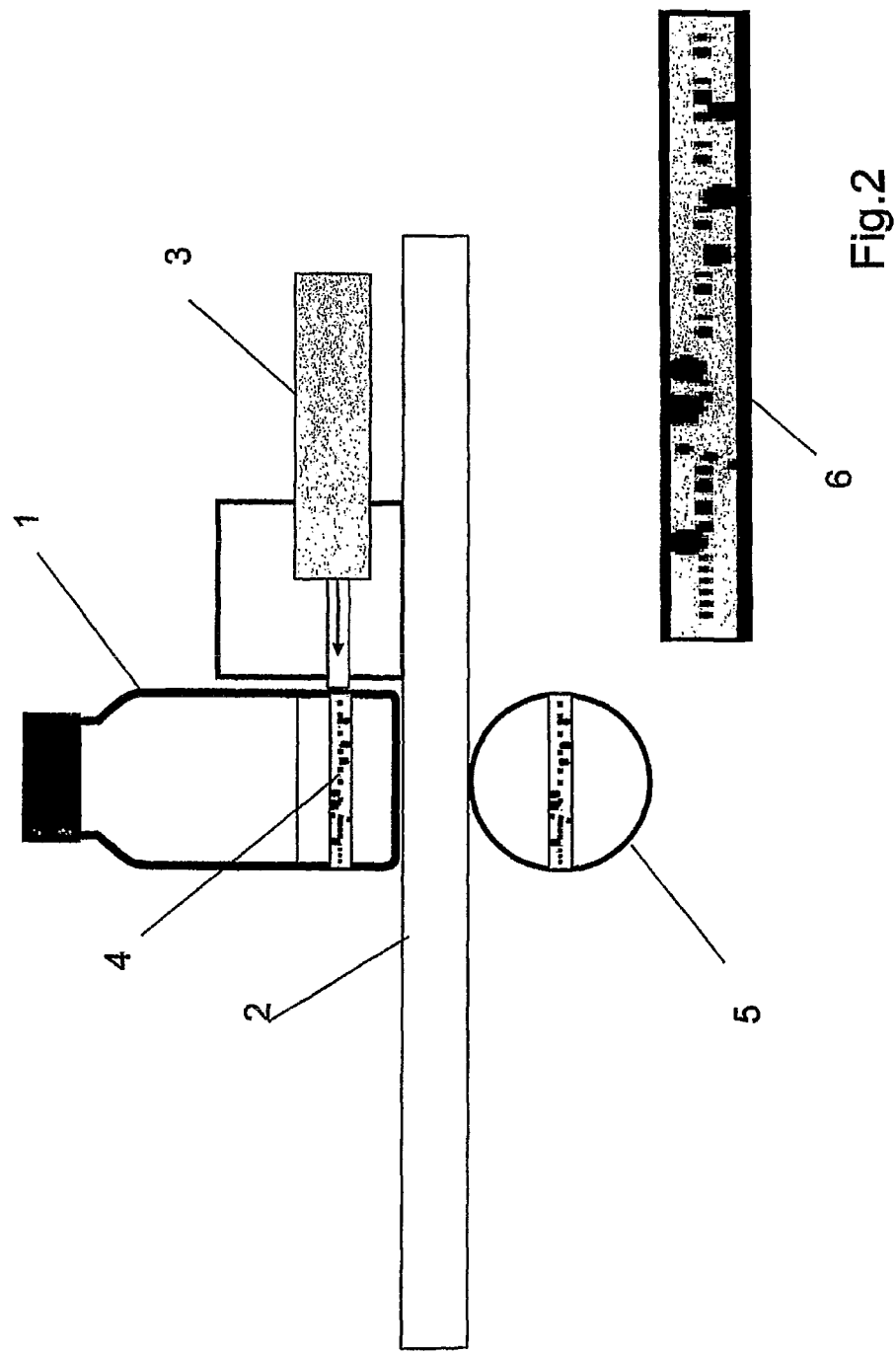

As shown in FIG. 2, the vials 1 may also be standing on the scanner bed 2. In this case the laser beam 4 emitted by laser 3 enters the solution through the side wall of the vial.

Figure 3:
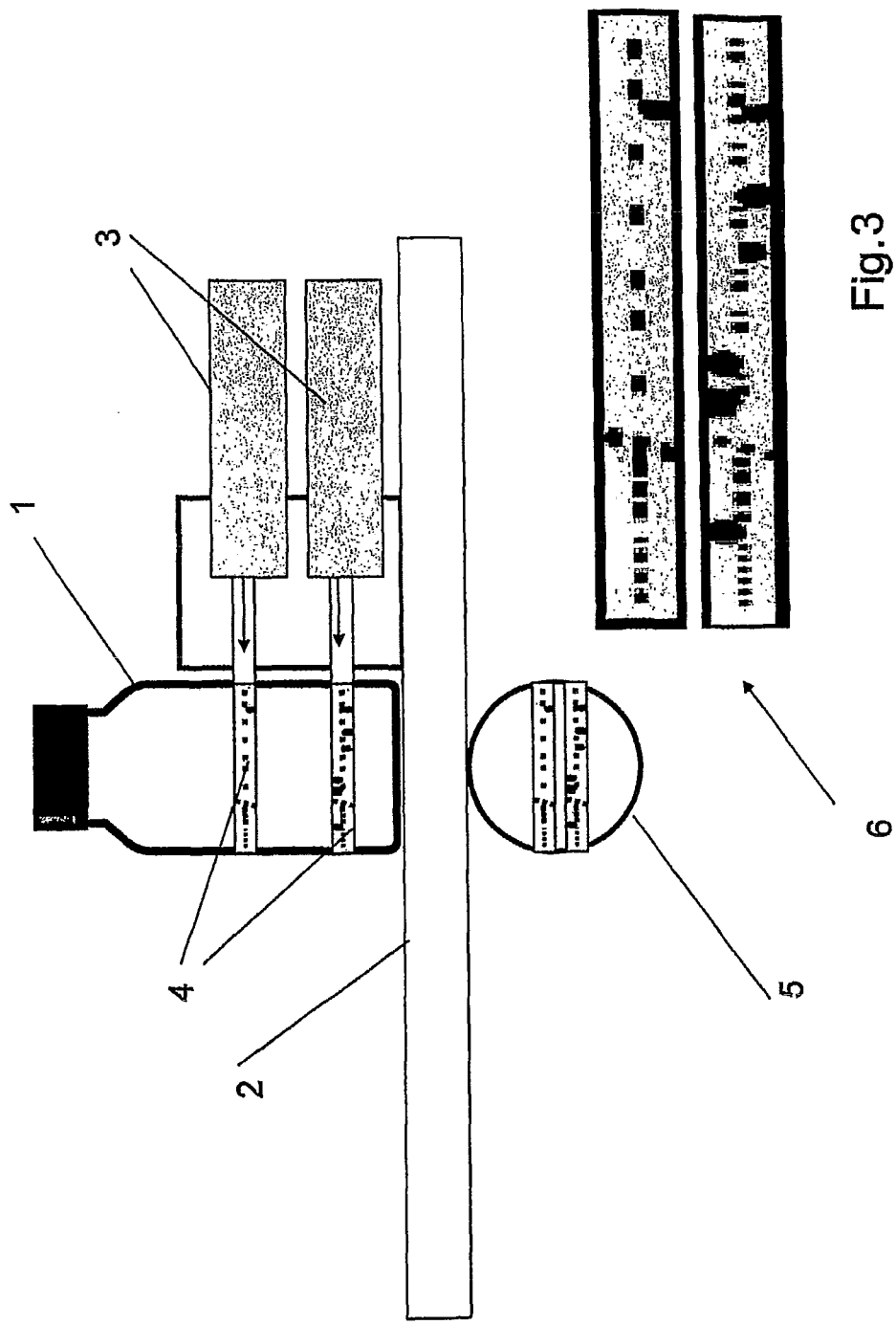

For detailed investigations an array of two or more lasers 3 is arranged to emit beams 4, preferably of different color, into or through the sample container 1 as shown in FIG. 3

Figure 4:
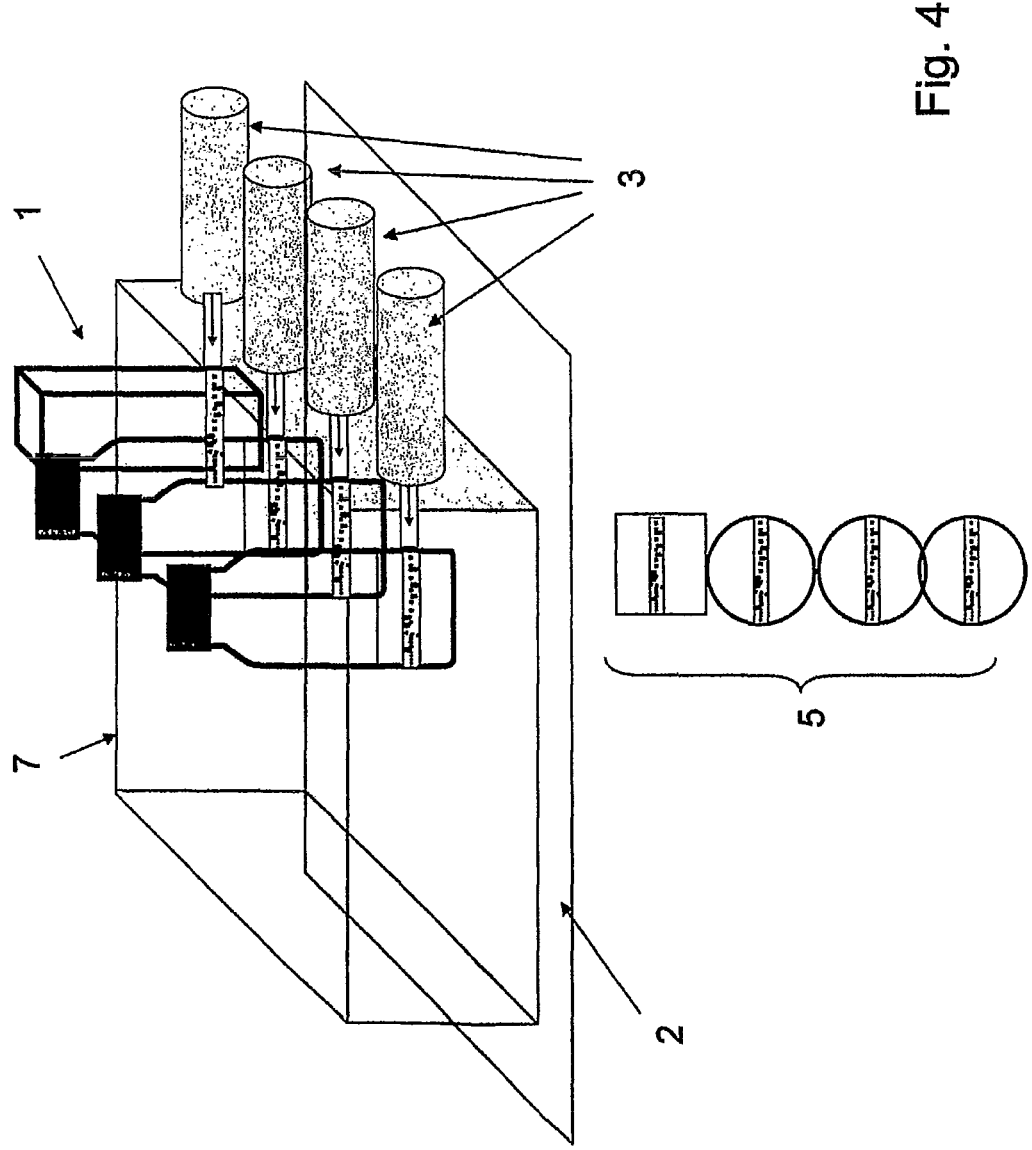
Figure 5:
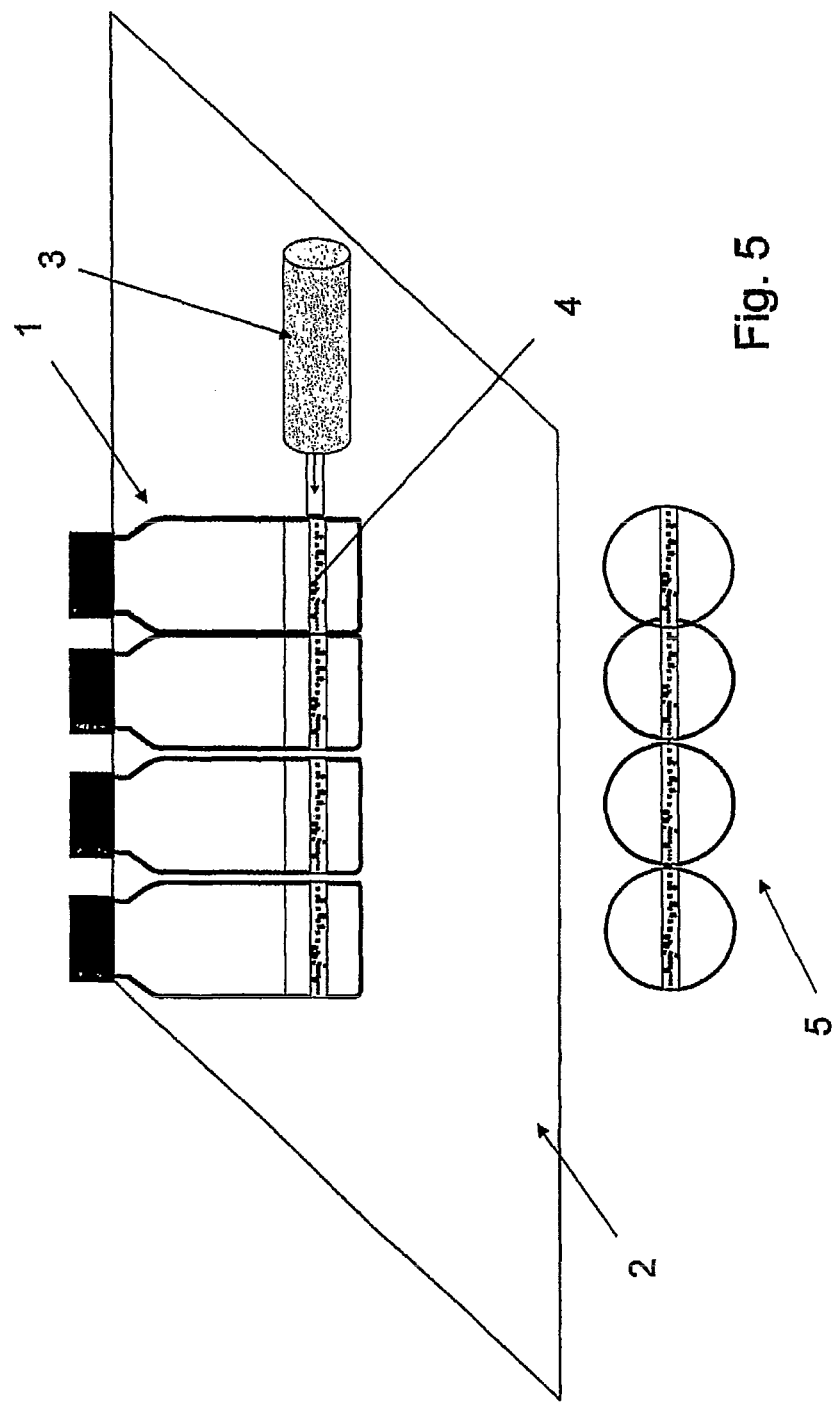

As shown in FIG. 4 a number of containers 1 which may also be of different type such as vials, cuvettes etc. are arranged in a sample chamber 7 in the shape of a frame positioned on a scanner surface 2. An array of lasers 3 emits laser beams 4 for simultaneously analyzing vials or sample cuvettes 1 located in the sample chamber. An alternative possibility is shown in FIG. 5 where a number of vials 1 positioned on a scanner surface 2 are simultaneously exposed to one laser beam 4. These arrangements allow the simultaneous analysis of a great number of samples.

Figure 6:
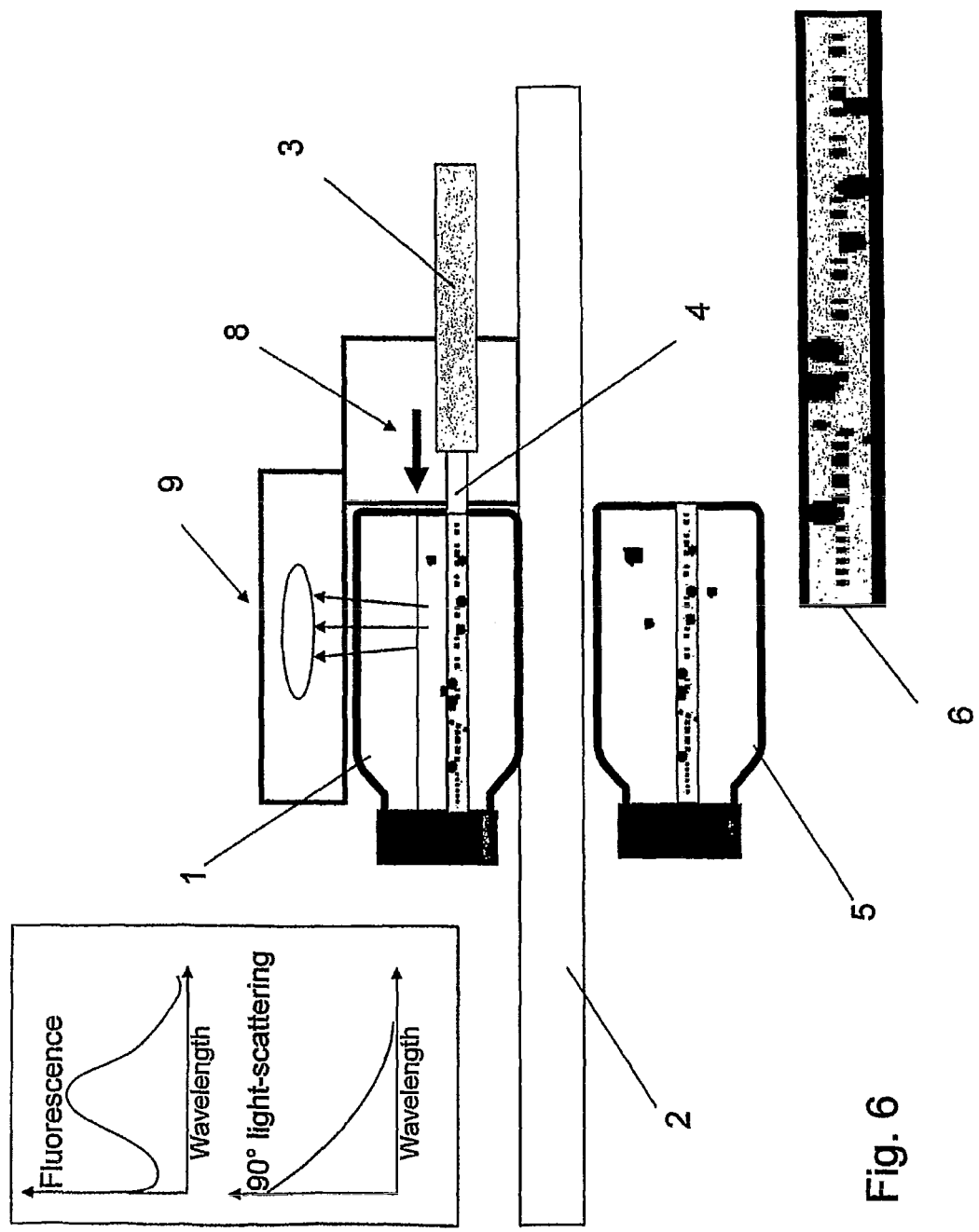

As shown in FIG. 6 the use of laser excitation may be combined with fluorescence spectroscopy. As in the examples described before a laser beam 4 emitted by a laser 3 is directed through a sample container 1 positioned on a scanner surface 2. Simultaneously excitation light 8, which may be transmitted by fiber optics from a spectrofluorimeter is guided into the sample and fluorescence light is received by a detector which may be fiber optics to the spectrofluorimeter.

Figure 7:
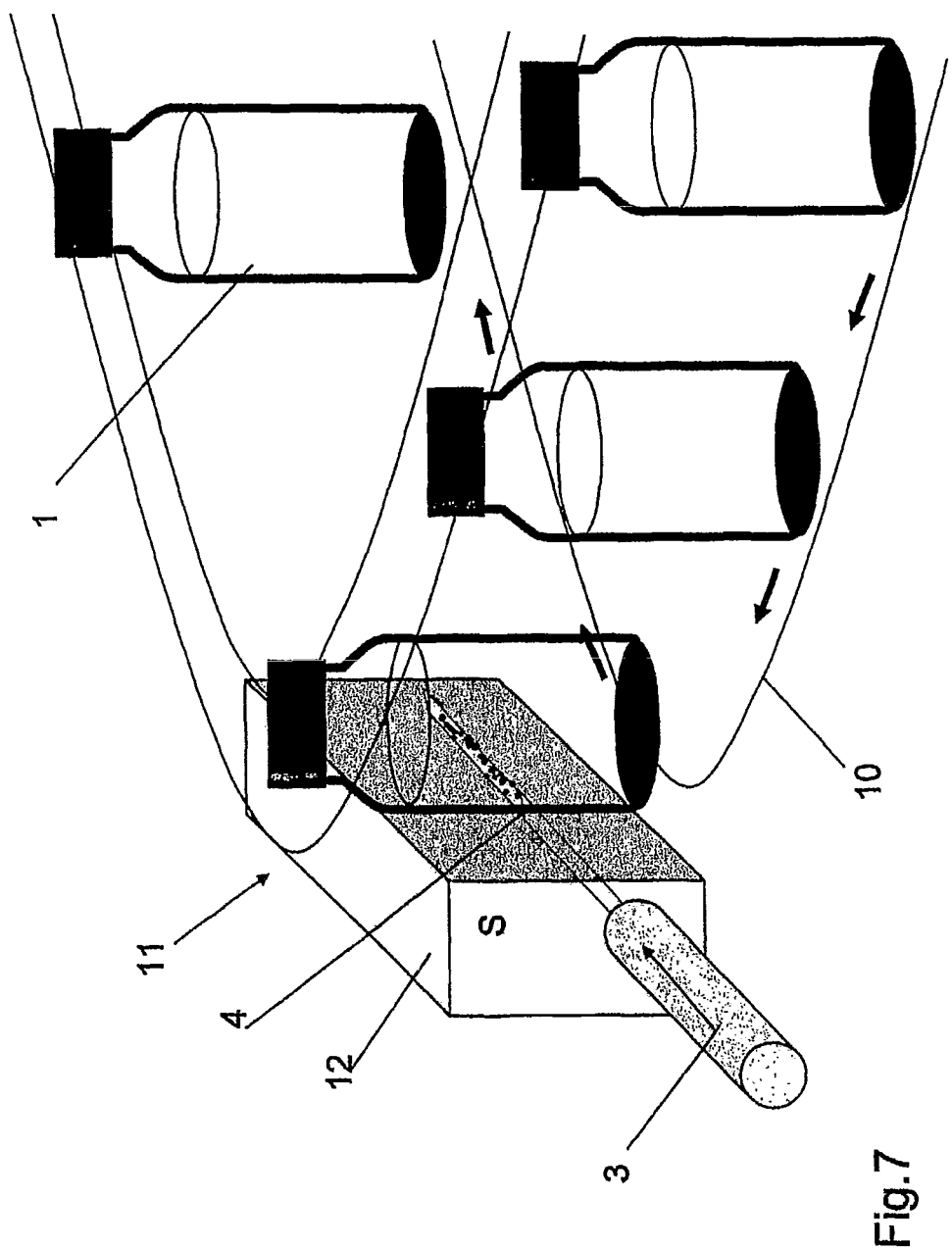

As shown in FIG. 7 a preferred embodiment of the invention is useful for continuous online detection of aggregates in vials containing e.g. solutions of pharmaceutical products. Vials 1 containing a product are moving along a production line 10 indicated schematically. The direction of movement is shown by arrows. At a measuring station 11 the vials pass in front of a vertically positioned scanner surface 12. While the vials pass the scanner they are exposed to a laser 4 emitted by a laser 3 located at the side of the line.

Figure 8:
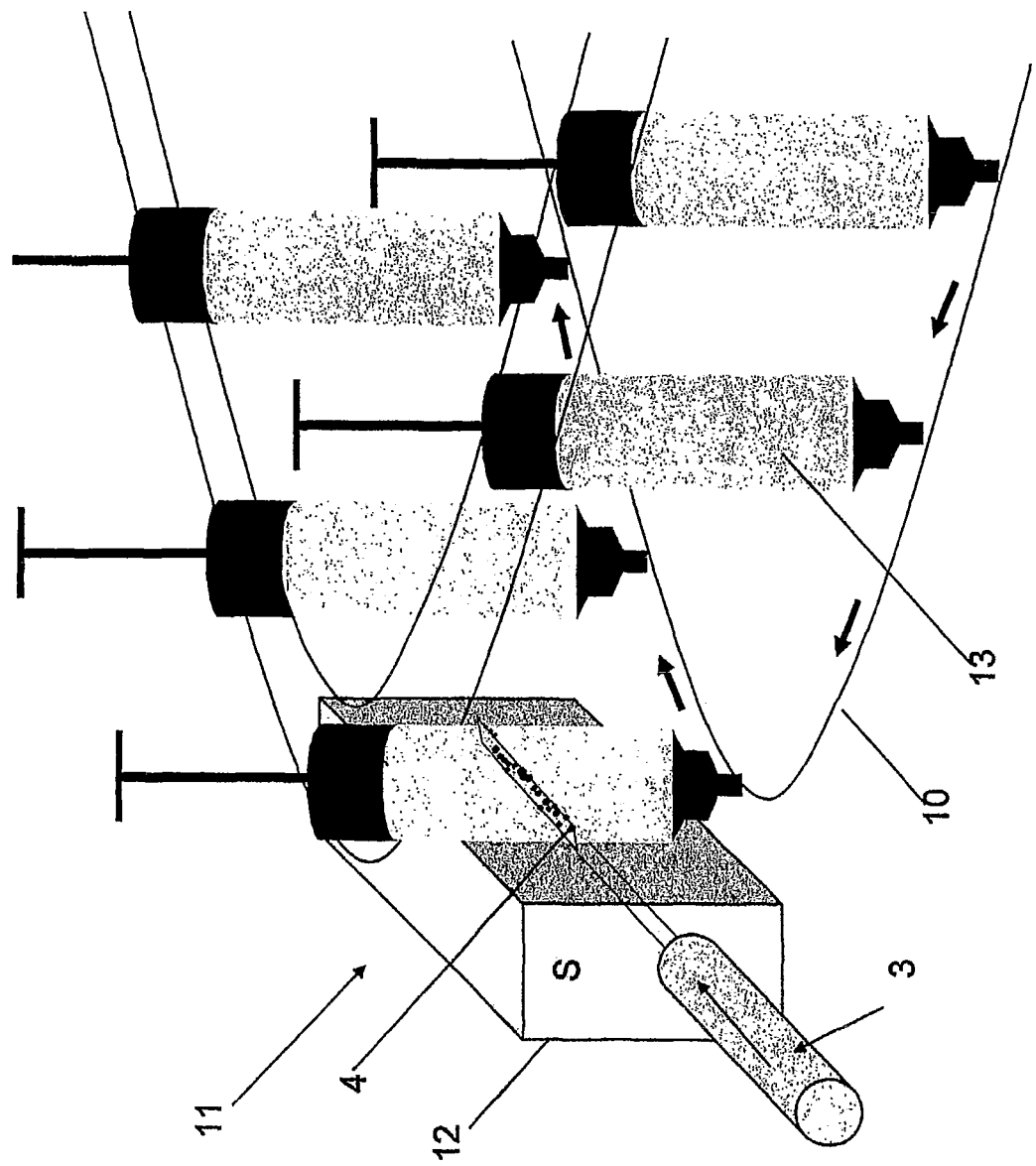

FIG. 8 shows a similar use for the detection of particles in pre-filled syringes 13 passing by a similar measuring station 11 where they are exposed to a beam 4 emitted by a laser 3. The laser beam 4 made visible by particulate matter in the solution is scanned by vertically arranged scanner 12. If particles such as protein aggregates and/or leachables are detected the vials or syringes are automatically separated.

Figure 9:
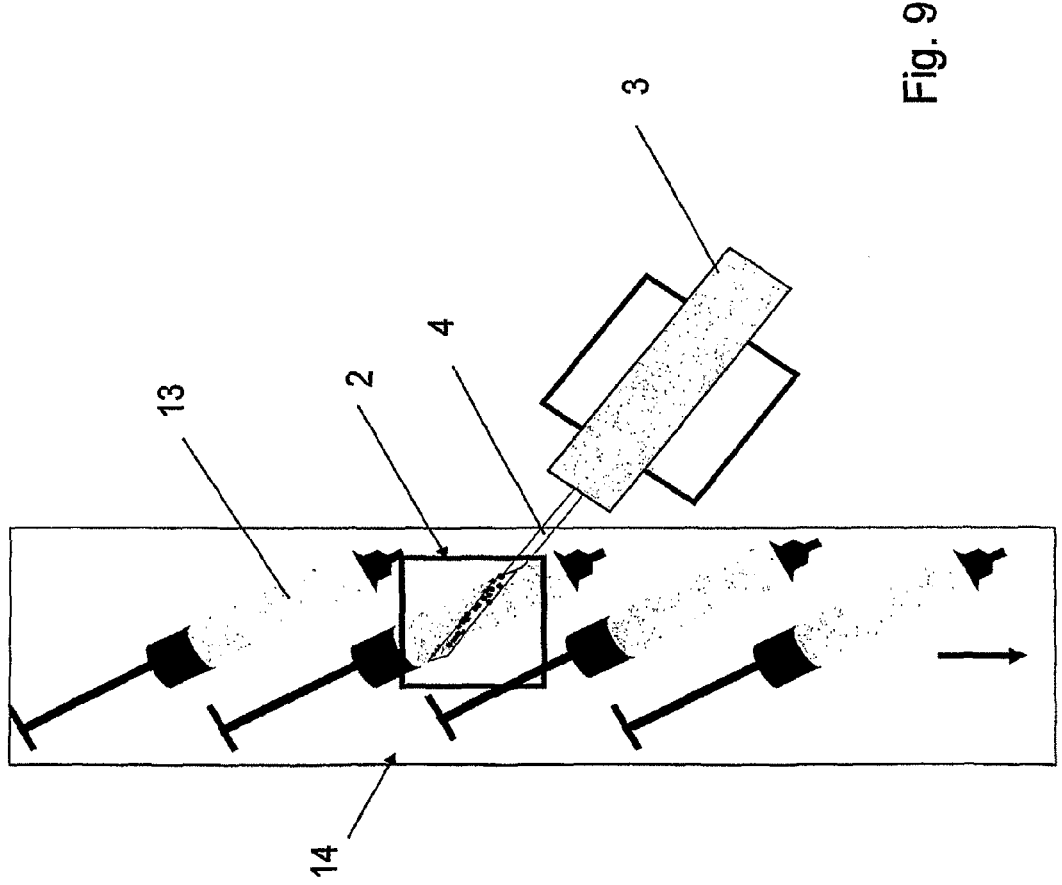

As shown in FIG. 9 the syringes 13 may also be transported lying on a belt 14 which moves over the scanner surface 2. A laser 3 is positioned at the side of the moving belt to emit a beam 4 which passes through the solution in the syringe.

Figure 10:
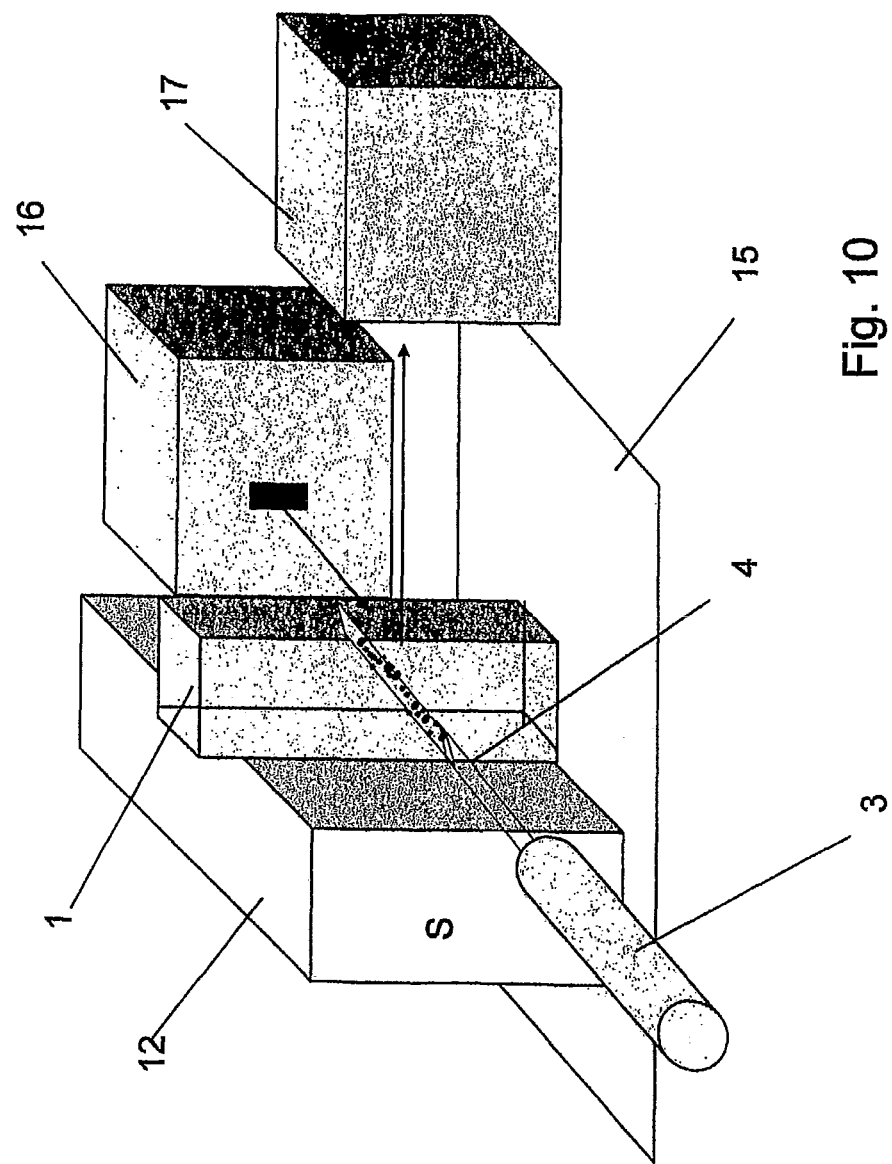

FIG. 10 shows equipment to be inserted in cuvette holder 15 for measuring fluorescence. As in the measuring station for online analysis of products a small vertical scanner is arranged at the side of the sample holding surface. A laser is positioned to emit a beam parallel to the scanner surface. A fluorescence excitation light source 16 is arranged opposite the laser and a detector 17 which may be fiber optics transmitting the fluorescence light to a spectrofluorimeter is arranged angularly displaced from the excitation beam. Similar equipment of this type may be adapted to other spectroscopic methods such as UV-VIS, circular dichroism, infrared or Raman spectrometry The fluorescence excitation frequently generates a visible effect in the sample which may also be recorded by the scanner even without a laser beam. Accordingly, the combination of a scanner with fluorescence measurement equipment is also one aspect of the present invention.

Figure 11:
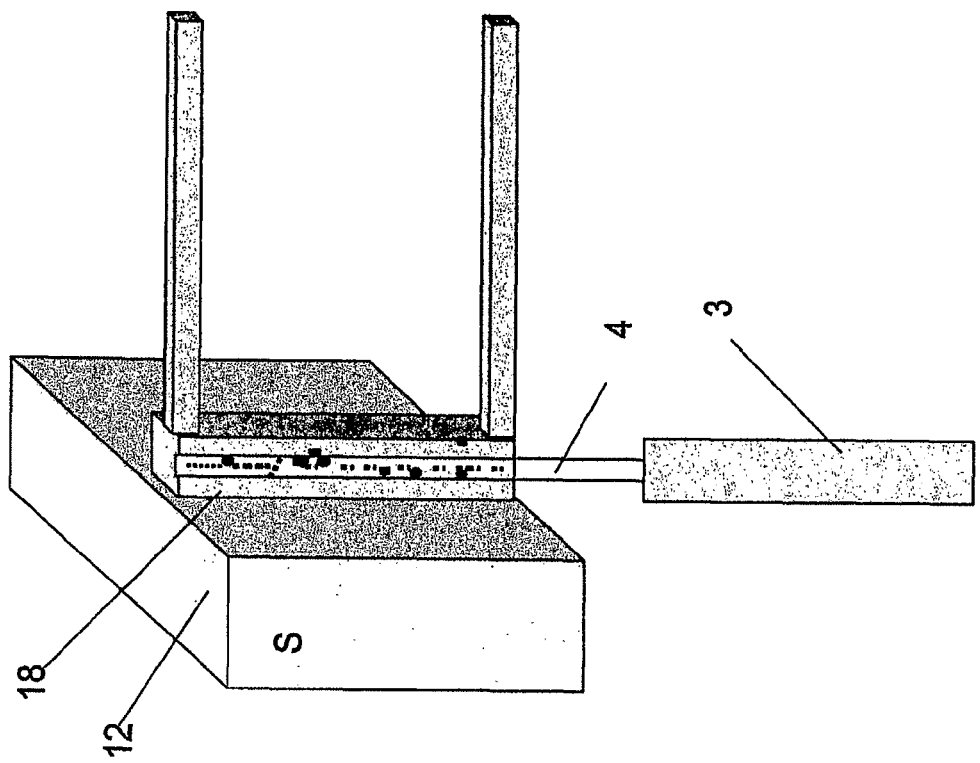
Figure 12:
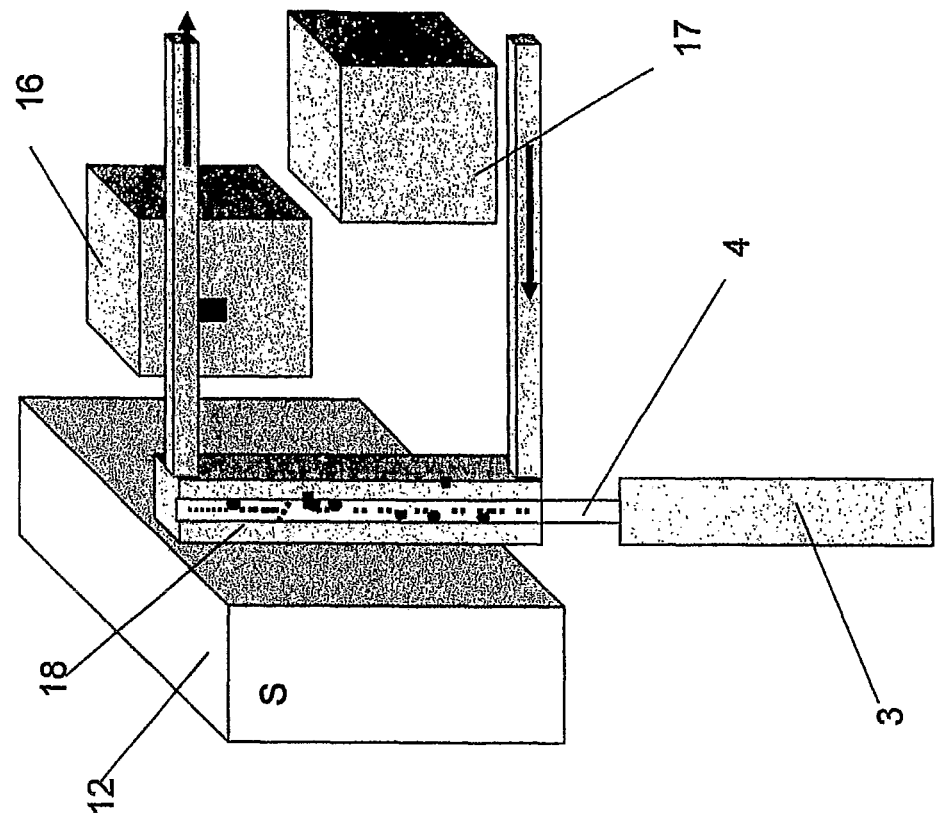

A further embodiment of the invention shown in FIG. 11 is a flow-through device 18 for online characterization of aggregates in different liquid chromatographic methods such as: size exclusion (SEC), high pressure liquid chromatography (HPLC), field flow fractionation (FFF), ion exchange chromatography, iso-electric focusing, or capillary zone electrophoresis (CZE). FIG. 12 shows the same arrangement with additional fluorescence measurement equipment as in the embodiment shown in FIG. 10.

Beside the detection and visualization of the particles by the scanner the online equipment may incorporate other detections such as fluorescence, UV, dynamic or static light scattering.

Figure 13:
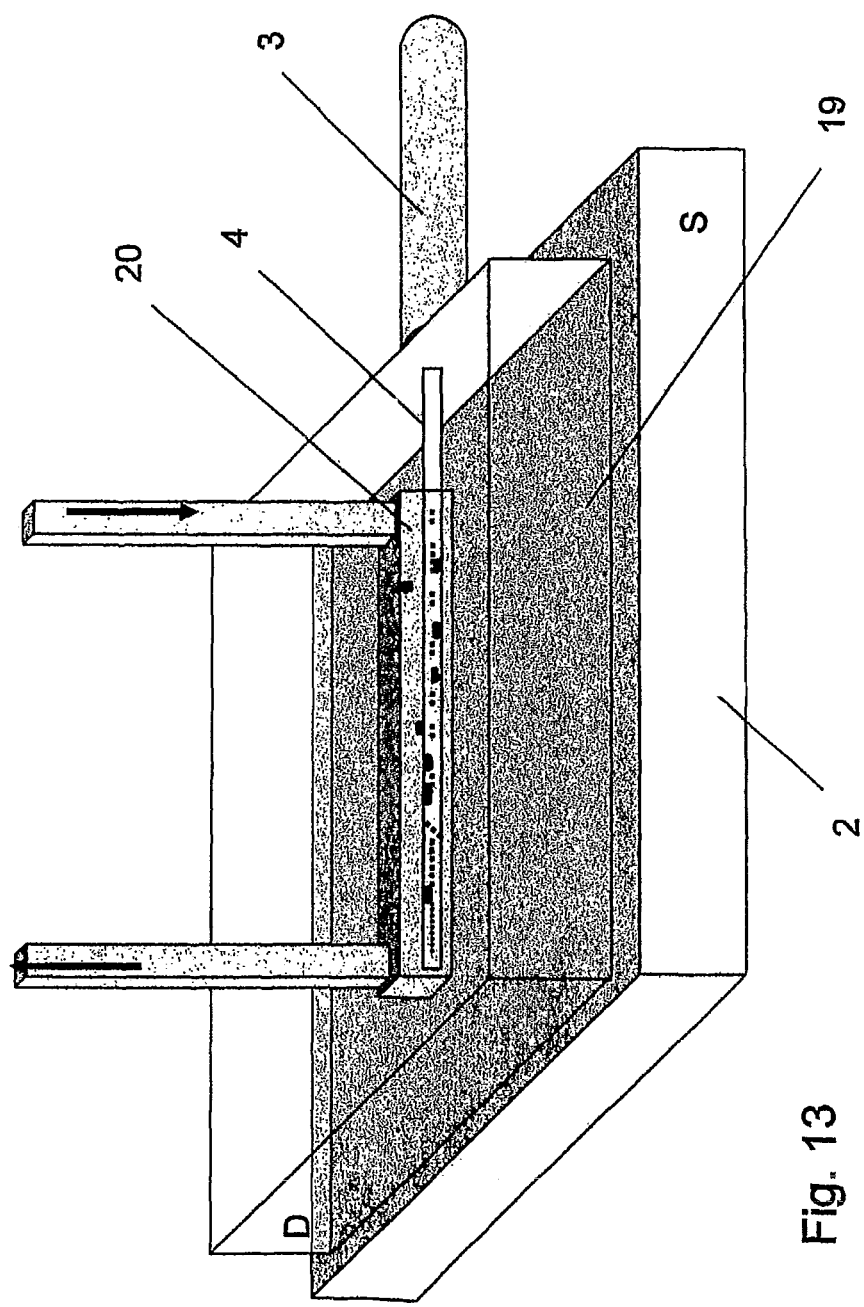

FIG. 13 shows the use of a laser and scanner as a part of a known dynamic or static light-scattering detector 19 having a flow-through capillary 20. The use of the visual scanner permits the analysis of large particles. The scanner 2 is positioned underneath the light scattering detector 19 whereas the laser is arranged at the side thereof. The system is especially useful for chromatography techniques such as filed flow fractionation.

The device shown in FIG. 14 is basically a box 21 to be placed on a scanner 2. It has an opening 22 for inserting a sample cuvette 23. The box contains a laser 24 arranged to direct a beam through the sample. The laser beam 25 is passing the sample parallel to the long side of the cuvette, but may also be directed under an angle, such as diagonal etc. Also contained and arranged at the side of the cuvette is a light source 26 emitting fluorescence excitation light such as from a spectrofluorimeter and UV-Vis monochromatic light. Above the cuvette a fluorescence emission detector 27 is positioned. And at the side opposite the light source a UV-Vis absorption detector 28 is arranged. With minor adaptations this device could of course also be used for multiple well plates.

The invention claimed is:

1. A method of determining parameters of individual contaminant particles contained in a given volume of a liquid solution in a container by means of a flat bed scanner, comprising the steps of
    placing the container with the solution onto or close to the bed of the flat bed scanner,
    guiding a laser beam through the container and the solution,
    digitally scanning the container with the solution therein while exposed to the laser beam to excite and visualize the individual contaminant particles in the solution, and
    producing an image of optical effects generated by the individual contaminant particles contained in the solution and scattering of the laser light, based on parameters of the individual contaminant particles in the solution, including size of the individual contaminant particles, morphology of the individual contaminant particles and number of the individual contaminant particles of a defined size in a given volume of the solution.

2. The method according to claim 1, wherein several laser beams are guided through the solution.

3. The method according to claim 2, wherein the laser beams are of different color.

4. The method according to claim 1, wherein a laser beam is simultaneously directed through several containers.

5. The method according to claim 1, wherein a fluorescence detection is combined with the laser excitation.

6. The method according to claim 1, wherein the content of containers is analyzed on-line.

7. The method according to claim 1, wherein the laser excitation is used in a flow-through arrangement.

8. An apparatus for performing the method according to any one of claims 1-7, comprising a light source positioned for guiding a laser beam onto or through a liquid solution in a container and a flat bed scanner arranged in a relative position to the sample for scanning the optical effect generated by the individual contaminant particles contained in the solution and scattering the laser light.

9. An apparatus for performing the method according to claim 1, comprising a light source positioned for guiding a laser beam onto or through a liquid solution in a container and a flat bed scanner arranged in a relative position to the solution for scanning the optical effect generated by the laser beam on or in the solution.

10. The method according to claim 1, wherein several laser beams are guided through the solution; and
    wherein a fluorescence detection is combined with the laser excitation.

* * * * *